United States Patent [19]

Romero-Sierra et al.

[11] 4,278,715

[45] Jul. 14, 1981

[54] PRESERVATION OF GREEN PLANT TISSUES

[75] Inventors: Cesar Romero-Sierra, Bath; John C. Webb, Kingston, both of Canada

[73] Assignee: Queen's University at Kingston, Kingston, Canada

[21] Appl. No.: 61,688

[22] Filed: Jul. 30, 1979

[30] Foreign Application Priority Data

Aug. 18, 1978 [CA] Canada ................................ 309654

[51] Int. Cl.³ .................... A01N 3/00; C09K 15/06
[52] U.S. Cl. ........................................ 428/22; 427/4; 252/400 R; 252/400 A; 252/407
[58] Field of Search .............. 427/4; 47/DIG. 2; 71/68; 252/400 R, 401, 400 A, 405, 407; 428/22

[56] References Cited

U.S. PATENT DOCUMENTS

| | | | |
|---|---|---|---|
| 1,484,656 | 2/1924 | Koropp | 42/DIG. 2 |
| 2,567,929 | 9/1951 | Fessenden | 427/4 |
| 2,606,843 | 8/1952 | Fessenden | 427/4 |
| 2,658,836 | 11/1953 | Fessenden | 427/4 |
| 2,698,809 | 1/1955 | Fessenden | 427/4 |
| 3,895,140 | 7/1975 | Fessenden | 42/DIG. 2 |

*Primary Examiner*—Sam Silverberg
*Attorney, Agent, or Firm*—Richard J. Hicks; Stanley E. Johnson

[57] ABSTRACT

A process for preserving green colored plant tissues while retaining the natural green color thereof, in which the tissues are immersed in a solution comprising: water, at least one monohydric alcohol, at least one preservative component selected from the group comprising lower carboxylic acids, di and tri hydric alcohols, and sufficient buffering and mordant reagents to control the pH and osmolality of said solution, so as to permanently retain said green color in said tissues. In a preferred embodiment the treated tissue is subjected to a secondary treatment in a holding solution comprising glycerin and water.

18 Claims, No Drawings

PRESERVATION OF GREEN PLANT TISSUES

This application relates to the preservation of green plant tissues and more particularly to a process and novel composition of matter for the preservation of the natural green colour in leaves, stems and the like of flowers, shrubs, trees and the like, and to the preserved product.

The preservation of flowers and other plants for museum specimens, for educational purposes in the natural sciences and elsewhere, for decorative and ornamental use, for displays and the like has been practised for many years and many processes for such preservation have been described in the literature. Attention is particularly directed to U.S. Pat. Nos. 2,658,929; 2,658,836 and 2,698,809 to Fessender and U.S. Pat. No. 2,971,242 to Malecki and to "Handbook of Plastic Embedding" E. C. Lutz (1969) p. 60–73 for descriptions of prior art processes for preservation of plant and animal tissues. None of the prior art processes are entirely satisfactory, however, because the delicate natural colours of flowers and other plant tissues tend to fade relatively quickly and the preserved products are extremely brittle, fragile and highly susceptible to damage in extremes of temperature or humidity. The treatment of the green parts of plants is particularly difficult because the chlorophyll content thereof is extremely sensitive and is very easily broken down to non-green (usually grey or brown) components. Indeed it is probably true to state that heretofore, preservation of naturally coloured green plant tissue has been impossible. A considerable advance in the art of preserving the natural colour and beauty of flowers is described in copending application for Letters Patent of Canada, Ser. No. 280,683 filed June 16, 1977 entitled "Flower Preservation" By Romero-Sierra and Webb and assigned to the present assignee, which application describes a treating solution in which flower specimens and the like may be treated. Such solution is highly effective for treatment of substantially all colours, but is not particularly well suited to the treatment of the green parts of plants, such as leaves, stems and the like.

It has now been found, however, that the green portions of plants, leaves and the like can be preserved, in substantially natural form, in a manner analogous to that employed for flowers as described in accordance with the aforementioned copending Canadian application. The treatment solution is, however, different as is the treatment mechanism.

It is, therefore, an object of the present invention to provide a process and composition of matter for the preservation of green plant tissues which is suitable for use with many varieties of green plants and which will result in naturally coloured specimens which will retain their freshness, flexibility and beauty for relatively long periods of time without the necessity of special handling and storage techniques.

By one aspect of this invention there is provided a solution for the preservation of naturally green coloured plant tissues consisting essentially of water, at least one monohydric alcohol, at least one preservative component selected from the group comprising lower carboxylic acids, and di and tri hydric alcohols, and sufficient buffering and mordant reagents to control the pH and osmolality of said solution so as to retain said green colour in said tissues.

By a preferred aspect of this invention there is provided a solution for the preservation of naturally green coloured plant tissues comprising:

(in amounts per liter of solution)
300–600 ml water
200–400 ml ethyl alcohol
20–60 ml ethylene glycol
0–7 ml glycerol
50–100 ml propionic acid
50–75 gms citric acid
0.5–2.5 gms cupric sulfate
3–6 gms magnesium sulphate
6–12 gms sodium sulfite.

By another aspect there is provided a process for preserving naturally green coloured plant tissues comprising immersing said tissues in a solution comprising water, at least one monohydric alcohol, at least one preservative selected from the group comprising lower carboxylic acids, di and tri hydric alcohols and sufficient buffering and mordant reagent to control the pH and osmolality of said solution so as to retain said green colour in said tissues for a period of time sufficient to effect exchange of water naturally contained in said tissues with said solution, thereby biologically preserving and fixing the green colour in said tissue.

In a preferred embodiment the treated tissue is subsequently immersed in a holding solution comprising glycerol and water for at least 10 days and air dried.

The invention will be described in more detail hereinafter with reference to the specific examples, it being appreciated that there are two principal objectives of the present invention (a) preservation of the green colour and (b) protection of the treated specimen. Leaves and the like may be prepared to be either flexible, for such uses as teaching and floral displays or relatively rigid so as to be free standing, for such uses as museum displays and the like.

While it is a relatively simple matter, as set forth in our copending application, to preserve flowers and the like, the preservation of green specimens presents an entirely different set of problems. Heretofore it has been found impossible to retain shape and colour in green succulent leaves and other relatively non-fibrous structures. The reason for this failure is relatively simple to comprehend since shape is maintained in plant tissue by two factors acting together. In the first instance, cellulose and similar materials form a relatively rigid framework into which the cells are arranged. The cells, however, are fully turgid only when filled with water and once this water is lost they collapse and the weight of tissues is too great for the fibres to support. When this happens wilting occurs. When the tissue dries out completely, rigidity is restored due to the loss of weight and also due to the loss of any lubrication between fibres. Succulents lack sufficient fibre to do this.

The dehydration process must be complete before the tissue is removed from its physical supporting medium. Failure to ensure this results in loss of shape and chemical reactions which ultimately result in tissue discolouration.

In the case of flowers, colour retention is far easier than in the case of green leaves because chlorophyll is a highly reactive and therefore sensitive substance. Flower pigments have evolved under circumstances which involve light reflection rather than light absorption and in this sense are relatively chemically inert by comparison with chlorophyll.

The problem therefore, is one in which dehydration must be effected in such a way as to retain original colour and shape and then treat the tissues so that they will last.

The cell walls of plants are composed of fibres which have a very high capacity to absorb moisture. Absorption of moisture from the air follows the diffusion of molecules of water vapour from the air down a water concentration gradient. This phenomenon is described by Ficks Law which, inter alia, shows that the rate of diffusion is a function of the water concentration in the tissue and the water concentration in the air. When these move in opposite directions i.e. the tissue gets drier and the air gets wetter, so the flux of water molecules gets greater. The ability of matter to absorb water is called its "water potential" and dried plant tissue has a very high "water potential". As tissue absorbs water, so its water potential is reduced and hence the amount of water held in tissue is a function of the atmospheric humidity.

Once dry tissue has absorbed water from the atmosphere, the ability of the fibres in the cell walls to retain their position vis-a-vis one another, fails, and the tissue collapses. With this water absorption the initiation of degradative processes is also seen which may be the result of endogenous enzyme reactions, direct chemical reactions or due to exogenous organisms such as saprophytic bacteria which "abound for this very purpose". The initiation of endogenous reactions following rehydration is possible since cell integrity would be lost with dehydration where membranes (as distinct from cell walls) were disrupted. On rehydration, a general mixing of cell contents would result in fairly widespread enzymic and nonenzymic chemical reactions.

In the case of green leaves the following chlorophyll derivatives have been described (Daley, "Methodology and Characterization of Lacustrine Chlorophyll Diagenesis" PhD Thesis Queen's University at Kingston, 1971).

(1) Pheophytins: Grey-brown in colour, they are produced under mild acid conditions when the centrally chelated magnesium atom is removed.

(2) Pheophorbides: Grey-brown in colour, they are formed when chlorophyllides (and occasionally) when pheophytins are acidified. Chemically they differ from chlorophylls since both the central magnesium atom and the phytol have been removed.

(3) Chlorophyllides: Green in colour they are produced in the presence of the enzyme chlorophyllase. They differ from chlorophyll since the phytol has been removed.

(4) Other forms include the chlorophyll isomers and allomers. Both these latter two forms are changes involving oxidation. Both these forms are green and spectrally identical but can be distinguished chromatographically.

Daley notes that "in killed leaves of higher plants, the actions of oxidative enzymic systems result in a . . . distinct form of allomerised chlorophyll, in which the $C_{10}$ hydrogen has been replaced by a methoxy group. Once formed, allomerised chlorophyll can be converted to the corresponding pheophytin, pheophorbide or chlorophyllide . . . ".

Many experiments have been conducted using many different approaches to the problem of retaining the natural green colour of chlorophyll or chlorophyll-derivative containing plants, ranging from drying, treating in microwave ovens, conformal coating and immersion in numerous treatment baths with little or no lasting success, particularly when the leaves are exposed to high light intensities and/or high humidity. It is believed that such treatments failed largely because of hydration problems which adversely affect the chlorophyll and derivatives thereof in the green tissues. The present inventors have, therefore, taken a fundamentally different approach to the problem and have made no attempt to dehydrate the green tissues but rather to effect an exchange process wherein the naturally contained water in the tissue is exchanged with a water based treatment solution containing sufficient chemical reagents to biologically preserve and environmentally fix the green colours. The treatment solution should also contain buffers and the like to modify the biologically harsh effects of the primary chemicals. Thus, it has been found that a suitable treatment solution for green plant tissues must contain four essential groups of chemicals which may be defined as:

(a) water;
(b) an exchange medium
(c) preservatives; and
(d) buffers, mordants and modifiers.

The group (c) preservatives may be further defined as:
(i) biological preservatives;
(ii) environmental fixers; and
(iii) biological fixatives.

Throughout this specification, when referring to "water" it is implicit that distilled water is normally employed, in order to ensure uniformity of results and to provide a readily controlled standard, but it will be appreciated that distillation is not an essential characteristic of the water employed, other forms such as deionized water being equally effective. The "exchange medium" used in the present inventions is normally one or more monohydric alcohols containing 1–6 carbon atoms. Such alcohols, particularly ethyl alcohol, isopropyl alcohol and tertiary butyl alcohol are known to have considerable dehydration properties and, without wishing to be bound by this explanation, it is believed that in the present invention the alcohol or mixtures of alcohols selected causes dehydration of the natural water contained in the plant tissue and the simultaneous replacement thereof by the chemical-containing water of the inventive solutions of the alcohols listed, tertiary butyl alcohol is extremely harsh and may damage leafy tissue and for this reason is normally used in admixture with a milder alcohol such as 1-propanol. Ethyl alcohol, on the other hand may be used alone.

As noted above the preservative elements of the solution fall into three broad categories, firstly as a biological or tissue preservative it has been found that lower carboxylic acids such as formic acid, acetic acid, or propionic acid, or mixtures thereof are effective. Secondly, as an environmental fixer, i.e. an agent which will give "body" to the preserved tissue and provide resistance to "weathering" it has been found that a dihydric alcohol such as glycol, and more particularly ethylene glycol, or a trihydric alcohol such as a glycerol (1,2,3-propanetriol) or mixtures thereof are highly effective. Thirdly, although not an essential ingredient, it is usually desirable to include a biological fixative the most common of which is formalin although other fixatives may also be used.

The fourth group of chemicals are generally referred to herein as "buffers, mordants and modifiers" and include citric acid, sodium phosphate dibasic, magnesium sulphate, cupric sulphate, chrome alum, and sodium sulfite and mixtures thereof in relatively small proportions. The amount of each chemical required depends upon the type of leaf being treated, the "exchange medium" being used and other factors. Some chemicals appear to act as mordants while others are buffers not only for pH but also for osmolality. While not considered critical it has been found that best results are obtained when the pH of the treatment bath is maintained in the range 6-8 i.e. substantially neutral.

Other minor ingredients may also be added as required. For example, a small amount of salicylic acid has been found beneficial to natural colour and in instances where the specimens are infected with fungus growths and the like the use of a fungicide such as Zephiran ® (benzalkonium chloride) has been found useful.

Particularly preferred treatment solutions comprise (in amounts per liter of solution)
300-600 ml water
200-400 ml ethyl alcohol
20-60 ml ethylene glycol
0-7 ml glycerol
50-100 ml propionic acid or formic acid
50-75 gms citric acid
0.5-2.5 gms cupric sulfate
3-6 gms magnesium sulphate
6-12 gms sodium sulfite
Other preferred solutions comprise:
400-600 ml water
100-150 ml 1-propanol
100-150 ml tert butyl alcohol
25-50 ml formalin
120-160 ml ethylene glycol
20-40 ml acetic acid
50-100 ml propionic acid
5-10 gms cupric sulfate
0.5-1.5 gms salicylic acid
0.5-2.0 gms chrome alum
1-10 drops Zephiran ®
and
500-700 ml water
80-150 ml sec butyl alcohol
20-40 ml formalin
50-70 ml ethylene glycol
100-140 ml glycerol
30-60 ml acetic acid
50-70 ml propionic acid
1-5 gms cupric sulfate
1-3 gms magnesium sulfate
1-5 gms sodium phosphate dibasic.

The procedures to be adopted for treatment of the plant tissue are simple and straightforward. Firstly a treating solution is prepared by mixing the required chemicals, preferably in the order as noted below, and then immersing the specimens in the treating solution, at ambient temperature, for 10 days to 2 weeks or even longer depending upon the specimen. For example most deciduous leaves require a relatively shorter period of time than evergreens and thick tough leaves such as holly may require as long as 30 days or even more. Very thick leaves, for example rubber leaves, may require even longer. Leaves of succulents and other species which tend to be very watery and with little fibrous structure (for example water cress) by reason of their species or method of culture are somewhat difficult to treat according to the present invention even if great care is taken with the selection of the exchange medium as it appears difficult to balance the rate of exchange of natural water with the treating solution. Generally, upon immersion in the bath the colour of the leaves changes, usually to a lighter green, then as the treatment solution replaces the natural water the colour reverts to an "ideal" colour and on continued immersion the colour darkens. Following treatment in the treating solution, the specimens may be air dried and stored for use as required. Such treated specimens are best used (for teaching or similar purposes) within 2 to 3 weeks as they tend to dry out after that time. If it is desired to preserve the specimens for later use (i.e. spring or summer leaves for use as teaching aids in mid winter) or for permanent display, secondary treatment in a "holding solution" is required. The holding solution is a glycerin/water solutions preferably containing 100-700 ml glycerin per liter of water. The specimens are merely immersed and soaked in the holding solution for 2-3 weeks, at ambient temperature and then air dried. Specimens so treated maintain their colour and flexibility for periods in excess of 1 year. In certain circumstances it may be desirable to store the specimens permanently in the holding solution, depending on the end use. There is, therefore, no practical limit to the treatment time in the holding solution.

EXAMPLE 1

A series of preserving solutions were prepared using mixtures of distilled water, monohydric alcohol, preservatives and buffers as hereinbefore defined and as listed below, each component being added in sequence so as to maintain the pH of the solution during mixing in the range of 6-8, in amounts per liter of solution as set forth in Table 1, below:

TABLE 1

| Component | Soln. A | Soln. B | Soln. C | Soln. D |
|---|---|---|---|---|
| Distilled water ml | 495 | 500 | 588 | 495 |
| 1-propanol ml | | 125 | | |
| tert-butyl alcohol ml | | 125 | | |
| sec-butyl alcohol ml | | | 118 | |
| ethyl alcohol ml (unmatured 95%) | 337 | | | 337 |
| formalin ml | | 36 | 29 | |
| ethylene glycol ml | 39 | 143 | 59 | |
| glycerol ml | 53 | | 118 | |
| formic acid ml | | | | 84 |
| acetic acid ml | | 28.5 | 44 | |
| propionic acid ml | 84 | 72 | 59 | |
| citric acid gm | 63 | | | 63 |
| cupric sulfate gm | 1.5 | 7.0 | 3.0 | 1.5 |
| magnesium sulfate gm | 4.2 | | 1.5 | 4.2 |
| sodium sulfite gm | 8.4 | | | 8.4 |
| salicylic acid gm | | 1.1 | | |
| sodium phosphate dibasic | | | 3.0 | |
| chrome alum | | 1.1 | | |
| Zephiran ® | | 2 drops | | |

EXAMPLE 2

Many green leaf samples, as set forth in Table II below, were soaked for 10 days to 2 weeks, at ambient temperature in baths containing solutions A, B, C and D prepared as in Example 1. After treatment the leaves were placed in a holding bath containing 650 ml white glycerin per 1000 ml distilled water for 2-3 weeks, then removed, air dried and evaluated for colour and flexibility.

TABLE II

| Leaf | Soln. A | Soln. B | Soln. C | Soln. D |
|---|---|---|---|---|
| Black Spruce | good green and flexible ↓ | good green somewhat darker than A and some tendency to "burn" ↓ | good green intermediate A and B, some burning and less "lively" (vibrant) green colour ↓ | good green similar to A but slightly brighter ↓ |
| White Spruce | ↓ | ↓ | ↓ | ↓ |
| White Pine | ↓ | ↓ | ↓ | ↓ |
| Jack Pine | ↓ | ↓ | ↓ | ↓ |
| Red Pine | ↓ | ↓ | ↓ | ↓ |
| White Cedar | ↓ | ↓ | ↓ | ↓ |
| Red Cedar | ↓ | ↓ | ↓ | ↓ |
| Lilac | ↓ | ↓ | ↓ | ↓ |
| Rose | ↓ | ↓ | ↓ | ↓ |
| Basswood | ↓ | ↓ | ↓ | ↓ |
| Horse Chestnut | ↓ | ↓ | ↓ | ↓ |
| Sugar Maple | ↓ | ↓ | ↓ | ↓ |
| Norway Maple | ↓ | ↓ | ↓ | ↓ |
| Silver Maple | ↓ | ↓ | ↓ | ↓ |
| Manitoba Maple | ↓ | ↓ | ↓ | ↓ |
| Crimson King Maple | ↓ | ↓ | ↓ | ↓ |
| Red Maple | ↓ | ↓ | ↓ | ↓ |
| White Birch | ↓ | ↓ | ↓ | ↓ |
| Rubber | satisfactory green after immersion for 30 days plus | — | — | |
| Holly | satisfactory green after 30 days immersion | darker green | — | — |
| Red Oak | fairly good green | browns | — | fairly good green |
| White Oak | browns | browns | — | |
| Thistle | — | — | — | better green than A |
| Flowering Crab | — | — | — | better green than A |
| Moss | — | — | darker green | — |

From Table II it is apparent that Solutions A and D are preferred for most varieties of green leaf as there is less tendency for burning and darkening, with solution A being the most preferred. Solution B may be considered marginal in many instances, possibly because of the strong and harsh dehydrating effects of tertiary butyl alcohol, even allowing for the modifying effects of the propanol. Solution C yields results intermediate A and B as sec-butyl alcohol is apparently not as harsh as tert-butyl alcohol.

It will be appreciated that many modifications to composition and process of the present invention may be effected by those skilled in the art without departing from the scope and ambit thereof. For example, it has been found possible to add the water and aliphatic alcohols to a mixture of the other components of the composition, with excellent results. This is advantageous from the point of view of marketing and transportation as the bulk of the composition comprises water and alcohol and it may be preferable to obtain appropriate supplies locally and mix it with a suitably packaged mixture of the remaining constituents. As has been previously noted, glycerin tends to soften the leaves and render them more pliable which is a desirable characteristic for many purposes or end uses but which is not necessarily required for permanent display purposes for example in museum exhibits. Thus when using Solutions A or D it may be desirable to reduce or even eliminate the glycerol element.

We claim:

1. A solution, for the preservation of naturally green coloured plant tissues, consisting essentially of 30%–70% by volume water; at least one monohydric alcohol; at least one preservative component selected from the group comprising lower carboxylic acids, and di- and tri-hydric alcohols; and sufficient buffering and mordant reagents to control the pH and osmolality of said solution so as to permanently retain said green colour in said tissues.

2. A solution, as claimed in claim 1 wherein said monohydric alcohol is selected from the group comprising ethyl alcohol, 1-propanol, secondary butanol and tertiary butanol.

3. A solution as claimed in claim 2 wherein di and tri-hydric alcohols are selected from the group comprising ethylene glycol and glycerin.

4. A solution as claimed in claim 1, wherein said lower carboxylic acid is selected from the group comprising formic acid, acetic acid and propionic acid.

5. A solution as claimed in claim 1, wherein said buffering and mordant reagents are selected from the group comprising citric acid, dibasic sodium phosphate, magnesium sulphate, cupric sulphate, chrome alum and sodium sulfite.

6. A solution as claimed in claim 1 additionally including a biological fixative.

7. A solution as claimed in claim 6 wherein said biological fixative is formalin.

8. A solution as claimed in claim 7 additionally including a fungicide.

9. A solution as claimed in claim 7 additionally including salicylic acid.

10. A solution as claimed in claim 1, and further comprising (in amounts per liter of solution)
    300–600 ml water
    200–400 ml ethyl alcohol
    20–60 ml ethylene glycol
    0–7 ml glycerol
    50–100 ml propionic acid
    50–75 gms citric acid
    0.5–2.5 gms cupric sulphate
    3–6 gms magnesium sulphate
    6–12 gms sodium sulfite.

11. A process for preserving naturally green coloured plant tissues comprising immersing said tissues in a solution comprising: 30%–70% by volume water; at least one monohydric alcohol; at least one preservative selected from the group comprising lower carboxylic acids, di- and tri-hydric alcohols, and sufficient buffering and mordant reagents to control the pH and osmolality of said solution so as to permanently retain said green colour in said tissues for a sufficient time to effect exchange of water naturally contained in said tissues with said solution, thereby biologically preserving and fixing the green colour in said tissue.

12. A process as claimed in claim 11 including immersing said treated tissue in a holding bath comprising glycerol and water for at least 10 days and air drying said tissues.

13. A process as claimed in claim 12 wherein the pH of said solution is maintained in the range between 6 and 8.

14. A process as claimed in claim 13 wherein said tissues are immersed in said bath at ambient temperature for at least 10 days.

15. A process as claimed in claim 14 wherein said solution comprises at least one monohydric alcohol selected from ethyl alcohol, 1-propanol, secondary butanol and tertiary butanol, at least one alcohol selected from the group comprising ethylene glycol and glycerin; at least one carboxylic acid from the group comprising formic acid, acetic acid and propionic acid; and at least one reagent selected from the group comprising citric acid, dibasic sodium phosphate, magnesium sulphate, cupric sulphate, chrome alum and sodium sulfite.

16. A process as claimed in claim 15 wherein said tissues are immersed in a solution comprising
300-600 ml water
200-400 ml ethyl alcohol
20-60 ml ethylene glycol
0-7 ml glycerol
50-100 ml propionic acid
50-75 gms citric acid
0.5-2.5 gms cupric sulphate
3-6 gms magnesium sulphate
6-12 gms sodium sulfite.

17. Green plant tissues treated with a solution as claimed in claim 1.

18. Green plant tissues produced by the process of claim 11.

* * * * *